(12) United States Patent
Aubert et al.

(10) Patent No.: US 6,228,799 B1
(45) Date of Patent: May 8, 2001

(54) COMPOSITION BASED ON CERIUM OXIDE AND ON ZIRCONIUM OXIDE WITH A HIGH SPECIFIC SURFACE AND A HIGH OXYGEN STORAGE CAPACITY, PROCESS OF PREPARATION AND USE IN CATALYSIS

(75) Inventors: Maryline Aubert, Angliers; Thierry Birchem, Paris; Gilbert Blanchard, Lagny-le-Sec, all of (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 09/180,716
(22) PCT Filed: May 9, 1997
(86) PCT No.: PCT/FR97/00829
  § 371 Date: Jun. 3, 1999
  § 102(e) Date: Jun. 3, 1999
(87) PCT Pub. No.: WO97/43214
  PCT Pub. Date: Nov. 20, 1997

(30) Foreign Application Priority Data

May 15, 1996 (FR) .................................................. 96 06051

(51) Int. Cl.⁷ ................................. B01J 23/00; B01J 8/00
(52) U.S. Cl. ........................ 502/304; 502/303; 502/302; 423/239.1
(58) Field of Search .................................. 502/304, 302, 502/303; 423/239.1

(56) References Cited

U.S. PATENT DOCUMENTS

| 5,693,299 | 12/1997 | Chopin et al. | 423/213.2 |
| 5,712,218 | 1/1998 | Chopin et al. | 502/304 |

FOREIGN PATENT DOCUMENTS

| 0605274 | 7/1994 | (EP) . |
| 0628515 | 12/1994 | (EP) . |
| 0629438 | 12/1994 | (EP) . |

*Primary Examiner*—Steven P. Griffin
*Assistant Examiner*—Jonas N. Strickland
(74) *Attorney, Agent, or Firm*—Burns, Doane, Swecker & Mathis, L.L.P.

(57) ABSTRACT

A composition based on cerium oxide and on zirconium oxide and, optionally, on a yttrium, scandium or rare-earth metal oxide. The cerium/zirconium atomic proportion is at least 1. The compound exhibits a specific surface, after calcination for 6 hours at 900° C. of at least 35 m²/g and an oxygen storage capacity at 400° C. of at least 1.5 ml of $O_2$/g. The composition is prepared by mixing, in a liquid medium, a cerium compound, a zirconium compound and, if appropriate, a yttrium, scandium or rare-earth metal compound; heating and calcining the precipitate obtained; and using a zirconium solution having an amount of base necessary to reach the equivalent point during an acid/base titration of the solution having a molar ratio of $OH^-$/$Zr \leq 1.65$. The composition thus obtained is used in the manufacture of multi-functional catalysts.

42 Claims, No Drawings

US 6,228,799 B1

COMPOSITION BASED ON CERIUM OXIDE AND ON ZIRCONIUM OXIDE WITH A HIGH SPECIFIC SURFACE AND A HIGH OXYGEN STORAGE CAPACITY, PROCESS OF PREPARATION AND USE IN CATALYSIS

FIELD OF THE INVENTION

The present invention relates to a composition based on cerium oxide and on zirconium oxide with a high specific surface and with a high oxygen storage capacity, to its process of preparation and to its use in catalysis, in particular for automobile catalysis.

BACKGROUND OF THE INVENTION

So-called multifunctional catalysts are currently used for the treatment of exhaust gases from internal combustion engines (automobile afterburning catalysis). Multifunctional catalyst is understood to mean catalysts capable of carrying out not only oxidation, in particular of carbon monoxide and hydrocarbons present in exhaust gases, but also reduction, in particular of nitrogen oxides also present in these gases ("three-way" catalysts). Zirconium oxide and cerium oxide today appear as two constituents which are particularly important and advantageous for this type of catalyst.

To be effective, these catalysts must first of all exhibit a high specific surface, even at high temperature. In addition, it is known that cerium makes possible a buffering power with respect to variations in the oxygen content of the gas mixture to be treated and thus makes it possible to improve the performance of the catalyst with respect to the three main pollutants, namely CO, HC and NOx. This buffering power is evaluated by the capacity to store oxygen in an oxidizing environment and to restore it in a reducing environment. However, this oxygen storage capacity decreases so much after exposure to high temperatures that the degree of conversion of the abovementioned pollutants may become insufficient.

For this reason, there exists a need for catalysts capable of being able to be used at high temperature and, in order to do so, exhibiting high stability of their specific surface combined, if possible, with stability of their oxygen storage capacity.

SUMMARY OF THE INVENTION

The subject of the invention is thus the development of a catalytic composition which can meet this need.

The composition according to a first embodiment of the invention is based on a cerium oxide and on a zirconium oxide in a cerium/zirconium atomic proportion of at least 1 and it is characterized in that it exhibits, after calcination for 6 hours at 900° C., a specific surface of at least 35 m$^2$/g and an oxygen storage capacity, measured at 400° C., of at least 1.5 ml of $O_2$/g.

According to a second embodiment of the invention, the composition is based on a cerium oxide, on a zirconium oxide and on an yttrium oxide in a cerium/zirconium atomic proportion of at least 1 and it is characterized in that it exhibits, after calcination for 6 hours at 900° C., a specific surface of at least 35 m$^2$/g and an oxygen storage capacity, measured at 400° C., of at least 1.5 ml of $O_2$/g.

According to a third embodiment of the invention, the composition is based, on the one hand, on a cerium oxide and on a zirconium oxide in a cerium/zirconium atomic proportion of at least 1 and, on the other hand, on at least one oxide chosen from scandium oxide and rare-earth metal oxides with the exception of cerium oxide and it is characterized in that it exhibits, after calcination for 6 hours at 900° C., a specific surface of at least 35 m$^2$/g.

In addition, the process for the preparation of the compositions according to the invention is of the type in which a mixture is prepared in liquid medium containing a cerium compound, a zirconium compound and, if appropriate, an yttrium, scandium or rare-earth metal compound; the said mixture is heated; the precipitate obtained is recovered and this precipitate is calcined, and it is characterized in that the abovementioned mixture is prepared by using a zirconium solution which is such that the amount of base necessary to reach the equivalent point during an acid/base titration of this solution confirms the condition that, as a molar ratio, $OH^-/Zr \leq 1.65$.

Other characteristics, details and advantages of the invention will become still more fully apparent on reading the following description, as well as the various concrete but non-limiting examples intended to illustrate it.

DETAILED DESCRIPTION

In the continuation of the description, specific surface is understood to mean the B.E.T. specific surface determined by nitrogen adsorption in accordance with ASTM standard D 3663-78 laid down from the Brunauer-Emett-Teller method described in the periodical "The Journal of the American Chemical Society, 60, 309 (1938)".

Rare-earth metal is understood to mean the elements from the group consisting of the elements of the Periodic Classification with an atomic number of between 57 and 71 inclusive.

The composition according to the invention can exist according to a number of embodiments but, in all cases, this composition is based on cerium oxide and on zirconium oxide and in a cerium/zirconium atomic proportion which is at least 1.

In the case of a first embodiment, the composition can be composed essentially of cerium and of zirconium. "Composed essentially" is understood to mean that the composition of the invention can exhibit its stability properties and in particular a catalytic activity in the absence of any other element of the oxide type commonly used in catalysis.

According to another embodiment of the invention, the composition additionally comprises yttrium oxide. It can be composed essentially, within the meaning of the term given above, of cerium oxide, yttrium oxide and zirconium oxide.

According to a third embodiment, the composition comprises at least one oxide chosen from rare-earth metal oxides and scandium oxide, with the exception of cerium oxide. It can, here again, be composed essentially, within the meaning of the term given above, of cerium oxide, of zirconium oxide and of the oxide or oxides of rare-earth metals and of scandium.

The rare-earth metal can be more particularly lanthanum, neodymium or praseodymium. Of course, the composition of the invention can comprise a number of rare-earth metal oxides or a combination of one or of a number of rare-earth metal oxides with scandium oxide.

In the case of the third embodiment, the composition can additionally comprise yttrium oxide.

The compositions of the invention can correspond to the formula $Ce_xZr_yM_zO_2$ in which M represents at least one element chosen from the group comprising yttrium, scandium and rare-earth metals, with the exception of cerium.

In the case where $z=0$, x can vary between 0.5 and 0.95, more particularly between 0.5 and 0.9 and more particularly still between 0.6 and 0.8, these values being inclusive and x and y being linked by the relationship x+y=1.

In the case where z is not zero, z preferably exhibits a value of at most 0.3 and which can be more particularly between 0.02 and 0.2 and, for these values of z, the x/y ratio can be between 1 and 19, more particularly between 1 and 9 and more particularly still between 1.5 and 4, the values other than 0 being inclusive and x, y and z being linked by the relationship x+y+z=1.

The compositions of the invention exhibit a specific surface, after calcination for 6 hours at 900° C. under air, of at least 35 $m^2/g$. This surface can more particularly be at least 40 $m^2/g$. It can more particularly still be at least 45 $m^2/g$.

The compositions of the invention can also exhibit specific surfaces which still remain significant even after calcination for 6 hours at 1000° C. These specific surfaces can be at least 14 $m^2/g$, more particularly at least 20 $m^2/g$ and more particularly still at least 30 $m^2/g$. The presence of an element such as yttrium, rare-earth metals and scandium, as described above, makes it possible to obtain compositions exhibiting the highest specific surfaces.

Another characteristic of the compositions of the invention is their oxygen storage capacity. This capacity, measured at 400° C., is at least 1.5 ml of $O_2/g$. It can more particularly be at least 1.8 ml of $O_2/g$ and more particularly still at least 2 ml of $O_2/g$. According to advantageous alternative forms of the invention, in particular for compositions exhibiting an element such as yttrium, rare-earth metals and scandium, this capacity can be at least 2.5 ml of $O_2/g$. The capacities given above are capacities measured with respect to products which were aged beforehand for 6 hours at 900° C.

The compositions of the invention can advantageously exist in the form of a solid solution. The X-ray diffraction spectra of these compositions in fact reveal, within the latter, the existence of a single homogenous phase. For the compositions which are the richest in cerium, this phase corresponds in fact to that of a crystalline ceric oxide $CeO_2$, the unit cell parameters of which are more or less offset with respect to a pure ceric oxide, thus reflecting the incorporation of zirconium and, if appropriate, of the other element in the crystal lattice of the cerium oxide and thus the preparation of a true solid solution.

The process for the preparation of the compositions of the invention will now be described.

The first stage of the process according to the invention consists in preparing a mixture in liquid medium, generally in the aqueous phase, containing at least one cerium compound, at least one zirconium compound and, if appropriate, an yttrium, scandium or rare-earth metal compound. This mixture is prepared by using a zirconium solution.

This zirconium solution can originate from the attack by acid on a reactant comprising zirconium. Mention may be made, as an appropriate reactant, of zirconium carbonate, hydroxide or oxide. The attack can be carried out with an inorganic acid, such as nitric acid, hydrochloric acid or sulphuric acid. Nitric acid is the preferred acid and the use of a zirconyl nitrate originating from the attack of nitric acid on a zirconium carbonate may thus be very particularly mentioned. The acid can also be an organic acid, such as acetic acid or citric acid.

According to the invention, this zirconium solution must exhibit the following characteristic. The amount of base necessary to reach the equivalent point during an acid/base titration of this solution must confirm the condition that, as a molar ratio, $OH^-/Zr \leq 1.65$. More particularly, this ratio can be at most 1.5 and more particularly still at most 1.3. Generally, the specific surface of the composition obtained has a tendency to increase when this ratio decreases.

The acid/base titration is carried out in a known way. In order for it to be carried out under optimum conditions, a solution which has been brought to a concentration of approximately $3 \times 10^{-2}$ mol per liter, expressed as elemental zirconium, can be titrated. A 1N sodium hydroxide solution is added thereto with stirring. Under these conditions, the equivalent point (change in the pH of the solution) is determined in a clear-cut way. This equivalent point is expressed by the $OH^-/Zr$ molar ratio.

Mention may particularly be made, as cerium compounds, of cerium salts such as cerium(IV) salts, such as nitrates or ceric ammonium nitrates for example, which are particularly well suited in this instance. Ceric nitrate is preferably used. The solution of cerium(IV) salts can contain cerium in the cerous state but it is preferable for it to contain at least 85% of cerium(IV). An aqueous ceric nitrate solution can, for example, be obtained by reaction of nitric acid with a ceric oxide hydrate prepared conventionally by reaction of a solution of a cerous salt, for example cerous nitrate, and of an aqueous ammonia solution in the presence of hydrogen peroxide. Use can also be made of a ceric nitrate solution obtained according to the process of electrolytic oxidation of a cerous nitrate solution as described in the document FR-A-2,570,087, which can constitute an advantageous starting material.

It will be noted here that the aqueous solution of cerium (IV) salts can exhibit a degree of initial free acidity, for example a normality varying between 0.1 and 4N. According to the present invention, it is just as possible to use an initial solution of cerium(IV) salts effectively exhibiting a degree of free acidity as mentioned above as a solution which would have been neutralized beforehand more or less exhaustively by addition of a base, such as for example an aqueous ammonia solution or alternatively a solution of alkali metal (sodium, potassium and the like) hydroxides, but preferably an aqueous ammonia solution, so as to limit this acidity. It is then possible, in the latter case, to define in practice a degree of neutralization (r) of the initial cerium solution by the following equation:

$$r = \frac{n3 - n2}{n1}$$

in which n1 represents the total number of moles of Ce(IV) present in the solution after neutralization; n2 represents the number of moles of $OH^-$ ions effectively necessary to neutralize the initial free acidity introduced by the aqueous cerium(IV) salt solution; and n3 represents the total number of moles of $OH^-$ ions introduced by the addition of the base. When the "neutralization" alternative form is implemented, use is made in all cases of an amount of base which absolutely must be less than the amount of base which would be necessary to obtain complete precipitation of the hydroxide species $Ce(OH)_4$ (r=4). In practice, the limit is therefore set at degrees of neutralization which do not exceed 1 and preferably still do not exceed 0.5.

The yttrium, scandium or rare-earth metal compounds are preferably compounds which are soluble in water in particular.

Mention may be made, as scandium or rare-earth metal compounds which can be used in the process of the invention, of, for example, the salts of inorganic or organic acids, for example of the sulphate, nitrate, chloride or acetate type. It will be noted that the nitrate is particularly well suited. These compounds can also be introduced in the form of sols. These solo can be obtained, for example, by neutralization by a base of a salt of these compounds.

The amounts of cerium, of zirconium and optionally of rare-earth metals, of yttrium and of scandium present in the mixture must correspond to the stoichiometric proportions required in order to obtain the final desired composition.

The initial mixture thus being obtained, it is then heated in accordance with the second stage of the process according to the invention.

The temperature at which this heat treatment, also known as thermohydrolysis, is carried out can be between 80° C. and the critical temperature of the reaction mixture, in particular between 80 and 350° C. and preferably between 90 and 200° C.

This treatment can be carried out, according to the temperature conditions used, either at normal atmospheric pressure or under pressure, such as, for example, the saturated vapour pressure corresponding to the temperature of the heat treatment. When the treatment temperature is chosen to be greater than the reflux temperature of the reaction mixture (that is to say generally greater than 100° C.), for example chosen between 150 and 350° C., the operation is then carried out by introducing the aqueous mixture containing the abovementioned species into an enclosed space (closed reactor more commonly known as an autoclave), the necessary pressure then resulting only from the heating alone of the reaction mixture (autogenous pressure). Under the temperature conditions given above, and in aqueous medium, it is thus possible to specify, by way of illustration, that the pressure in the closed reactor varies between a value greater than 1 bar ($10^5$ Pa) and 165 bar ($165 \times 10^5$ Pa), preferably between 5 bar ($5 \times 10^5$ Pa) and 165 bar ($165 \times 10^5$ Pa). It is of course also possible to exert an external pressure which is then added to that resulting from the heating.

The heating can be carried out either under an air atmosphere or under an inert gas atmosphere, preferably nitrogen.

The duration of the treatment is not critical and can thus vary within wide limits, for example between 1 and 48 hours and preferably between 2 and 24 hours.

On conclusion of the heating stage, a solid precipitate is recovered which can be separated from its mixture by any conventional solid/liquid separation technique, such as, for example, filtration, settling, draining or centrifuging.

It may be advantageous, after the heating stage, to introduce a base, such as, for example, an aqueous ammonia solution, into the precipitation mixture. This makes it possible to increase the recovery yields of the precipitated species.

It is also possible, in the same way, to add hydrogen peroxide after the heating stage.

The product as recovered can then be subjected to washings with water and/or with aqueous ammonia, at a temperature between ambient temperature and the boiling temperature. In order to remove the residual water, the washed product can finally, optionally, be dried, for example in air, at a temperature which can vary between 80 and 300° C. and preferably between 100 and 150° C., drying being continued until a constant weight is obtained.

It will be noted that it is of course possible, after recovery of the product and optional addition of the base or of hydrogen peroxide, to repeat a heating stage as described above one or a number of times, in an identical or nonidentical way, by then again placing the product in liquid medium, in particular in water, and by carrying out, for example, heat treatment cycles.

In a last stage of the process, the recovered precipitate, optionally after washing and/or drying, is then calcined. According to a specific embodiment, it is possible, after the thermohydrolysis treatment and optionally after again placing the product in liquid medium and an additional treatment, directly to dry the reaction mixture obtained by atomization.

The calcination is carried out at a temperature generally of between 200 and 1200° C. and preferably between 300 and 900° C. This calcination temperature must be sufficient to convert the precursors to oxides and it is also chosen as a function of the temperature of subsequent use of the catalytic composition, it being taken into account that the specific surface of the product becomes smaller as the calcination temperature employed becomes higher. The duration of the calcination can, for its part, vary within wide limits, for example between 1 and 24 hours and preferably between 4 and 10 hours. The calcination is generally carried out under air but a calcination carried out, for example, under an inert gas is very clearly not excluded.

The compositions of the invention as described above or as obtained in the processes mentioned above are provided in the form of powders but they can optionally be shaped in order to be provided in the form of granules, balls, cylinders or honeycombs of variable sizes. These compositions can be applied to any support commonly used in the field of catalysis, that is to say in particular thermally inert supports. This support can be chosen from alumlina, titanium oxide, cerium oxide, zirconium oxide, silica, spinels, zeolites, silicates, crystalline silicoaluminium phosphates or crystalline aluminium phosphates. The compositions can also be used in catalytic systems comprising a coating (wash coat), based on these compositions and with catalytic properties, on a substrate of the metal or ceramic monolith type, for example. The coating can itself also contain a support of the type of those mentioned above. This coating is obtained by mixing the composition with the support, so as to form a suspension which can subsequently be deposited on the substrate.

These catalytic systems and more particularly the compositions of the invention can have a great many applications. They are therefore particularly well suited to, and thus usable in, the catalysis of various reactions such as, for example, dehydration, hydrosulphurization, hydrodenitrification, desulphurization, hydrodesulphurization, dehydrohalogenation, reforming, steam reforming, cracking, hydrocracking, hydrogenation, dehydrogenation, isomerization, dismutation, oxychlorination, dehydrocyclization of hydrocarbons or other organic compounds, oxidation and/or reduction reactions, the Claus reaction, treatment of exhaust gases from internal combustion engines, demetallation, methanation or the shift conversion.

In the case of these uses in catalysis, the compositions of the invention are employed in combination with precious metals. The nature of these metals and the techniques for the incorporation of the latter in these compositions are well known to the person skilled in the art. For example, the metals can be platinum, rhodium, palladium or iridium and they can, in particular, be incorporated in the compositions by impregnation.

Among the uses mentioned, the treatment of exhaust gases from internal combustion engines (automobile afterburning catalysis) is a particularly advantageous application.

For this reason, the invention also relates to the use of a catalytic composition or of a catalytic system as described above in the manufacture of a catalyst for automobile afterburning.

Examples will now be given. The results with respect to the specific surfaces, the oxygen storage capacity and the calcination conditions (temperature and atmosphere) are given in the tables which follow the examples.

Description of the test which makes it possible to quantify the oxygen storage

The buffering power of a composition with respect to oxygen is evaluated by its ability to store oxygen in an oxidizing environment and to restore it in a reducing environment. The test evaluates the capacity of the composition to successively oxidize pulses of carbon monoxide and to consume pulses of oxygen in order to reoxidize the composition. The method employed is known as alternating.

The carrier gas is pure helium at a flow rate of 10 1/h. Injections are made via a loop containing 16 ml of gas. The pulses of CO are produced by using a gas mixture containing 5% of CO diluted in helium, whereas the pulses of $O_2$ are produced from a gas mixture containing 2.5% of $O_2$ diluted in helium. The gases are analysed by chromatography using a thermalconductivity detector.

The amount of oxygen consumed makes it possible to determine the oxygen storage capacity. The value characteristic of the oxygen storage power is expressed in ml of oxygen (under standard temperature and pressure conditions) per gram of product introduced and it is measured at 400° C. The measurements of oxygen storage power given in the table which follows are carried out with respect to products pretreated at 900° C. under air for 6 hours in a muffle furnace.

EXAMPLE 1

This example illustrates the preparation of a mixed oxide of formula $Ce_{0.62}Zr_{0.38}O_2$.

A ceric nitrate solution and a zirconyl nitrate solution are mixed in the stoichiometric proportions required to obtain the mixed oxide above. The zirconyl nitrate solution was obtained by attack on a carbonate using concentrated nitric acid. The solution corresponds, within the meaning defined above, to the condition that, as a molar ratio, $OH^-/Zr=0.94$.

The concentration of this mixture (expressed as oxide of the various elements) is adjusted to 80 g/l. This mixture is then brought to 150° C. for 4 hours.

An aqueous ammonia solution is then added to the reaction mixture so that the pH is greater than 8.5. The reaction mixture thus obtained is brought to boiling point for 2 hours. After separating by settling and then drawing off, the solid product is resuspended and the mixture thus obtained is treated for 1 hour at 100° C. The product is then filtered and then calcined at the temperature shown in the table of the results.

EXAMPLE 2

This example illustrates the preparation of a mixed oxide of formula $Ce_{0.65}Zr_{0.31}Nd_{0.04}O_2$.

A ceric nitrate solution, preneutralized by addition of $NH_4OH$ such that r=−0.22 (r being as defined above), a neodymium nitrate solution and a zirconyl nitrate solution, which corresponds, within the meaning defined above, to the condition that, as a molar ratio, $OH^-/Zr=1.17$, are mixed in the stoichiometric proportions required to obtain the mixed oxide above.

The procedure then followed is identical to that of Example 1 as far as the treatment stage for 1 hour at 100° C. The reaction mixture thus obtained is dried by atomization and then calcined at the temperature shown in the table of the results.

EXAMPLE 3

This example illustrates the preparation of a mixed oxide of formula $Ce_{0.645}Zr_{0.30}Y_{0.055}O_2$.

The mixing of the solutions is the same as in Example 2, apart from the stoichiometric proportions, neodymium nitrate being replaced by yttrium nitrate.

The procedure then followed is identical to that of Example 2.

EXAMPLE 4

This example illustrates the preparation of a mixed oxide of formula $Ce_{0.65}Zr_{0.31}La_{0.04}O_2$.

The mixing of the solutions and the procedure followed are the same as in Example 2, neodymium nitrate being replaced by lanthanum nitrate.

EXAMPLE 5

This example illustrates the preparation of a mixed oxide of formula $Ce_{0.66}Zr_{0.30}Pr_{0.04}O_2$.

The mixing of the solutions and the procedure followed are the same as in Example 2, neodymium nitrate being replaced by praseodymium nitrate.

EXAMPLE 6

This example illustrates the preparation of a mixed oxide of formula $Ce_{0.53}Zr_{0.37}La_{0.10}O_2$.

A ceric nitrate solution, a lanthanum nitrate solution and a zirconyl nitrate solution are mixed in the stoichiometric proportions required to obtain the mixed oxide above. The zirconyl nitrate solution corresponds, within the meaning defined above, to the condition that, as a molar ratio, $OH^-/Zr=1.17$.

The procedure then followed is identical to that of Example 1.

EXAMPLE 7

This example illustrates the preparation of a mixed oxide of formula $Ce_{0.525}Zr_{0.315}Pr_{0.16}O_2$.

A ceric nitrate solution, preneutralized by addition of $NH_4OH$ such that r=−0.34, a praseodymium nitrate solution and a zirconyl nitrate solution, which corresponds, within the meaning defined above, to the condition that, as a molar ratio, $OH^-/Zr=1.17$, are mixed in the stoichiometric proportions required to obtain the mixed oxide above.

The procedure then followed is identical to that of Example 2.

EXAMPLE 8

This example illustrates the preparation of a mixed oxide of formula $Ce_{0.535}Zr_{0.373}La_{0.047}Nd_{0.045}O_2$.

The procedure then followed is identical to that of Example 1 but a zirconyl nitrate solution, which corresponds, within the meaning defined above, to the condition that, as a molar ratio, $OH^-/Zr=1.17$, is used.

COMPARATIVE EXAMPLE 9

This example illustrates the preparation according to the prior art of a mixed oxide of cerium, of zirconium and of yttrium of formula $Ce_{0.65}Zr_{0.30}Y_{0.05}O_2$.

A ceric nitrate solution and a zirconyl nitrate solution, which corresponds, within the meaning defined above, to the condition that, as a molar ratio, $OH^-/Zr=1.80$, and an yttrium nitrate solution are mixed with stirring in the stoichiometric proportions required to obtain the mixed oxide above.

The mixture is then heat treated at 150° C. for 4 hours. On conclusion of this treatment, an aqueous ammonia solution is introduced into the suspension obtained so as to bring the pH to 9.5, the whole mixture then being stirred for 30 minutes in order to homogenize.

A precipitate is then recovered by filtration, is subsequently superficially dried and is then resuspended in water. This suspension is then heated at 100° C. for 1 hour.

The product is again filtered, then dried in an oven at 120° C. and finally calcined at 900° C. for 6 hours.

COMPARATIVE EXAMPLE 10

This example illustrates the preparation according to the prior art, by precipitation, of a mixed oxide of cerium and of zirconium of formula $Ce_{0.765}Zr_{0.235}O_2$.

A cerous nitrate solution and a zirconyl nitrate solution are mixed in the stoichiometric proportions required to obtain the mixed oxide above. The concentration as oxide of the elements is adjusted to 172 g/l.

This mixture thus obtained is added over 30 minutes to a solution containing aqueous ammonia, water and hydrogen peroxide. The product thus obtained is washed a number of times with demineralized water via a series of separations by settling and removals of the wash liquors. The product is subsequently filtered and then calcined at 900° C. for 6 hours.

EXAMPLE 11

This example illustrates the synthesis of a mixed oxide of composition $Ce_{0.657}Zr_{0.306}Pr_{0.037}O_2$ from a zirconyl nitrate solution, obtained by dissolution of a zirconyl carbonate in a nitric acid solution, which corresponds, within the meaning defined above, to the condition that, as a molar ratio, $OH^-/Zr=0.86$.

An aqueous solution containing cerium(IV) nitrate (non-preneutralized), praseodymium nitrate and zirconyl nitrate is prepared, in the stoichiometric proportions required to obtain the mixed oxide above, such that the total concentration as oxide of the mixture is 80 g/l.

The mixture is then heat treated at 150° C. for 4 hours in an autoclave with constant stirring.

On conclusion of this treatment, aqueous ammonia is introduced into the suspension obtained so as to bring the pH to 9. The whole mixture is then maintained at 100° C. for 2 hours.

The mother liquors are drawn off. The product is then resuspended and the pH of the suspension is readjusted to 9 by addition of the necessary amount of aqueous ammonia. The mixture is kept stirring for 1 hour at 100° C. On conclusion of this washing operation, the product is again filtered, then dried overnight in an oven at 110° C. and then calcined at the temperature shown in the table of the results.

TABLE 1

| Example | S.S.* in m²/g 900° C. | S.S.& in m²/g 1000° C. | OSC** in ml O₂/g |
|---|---|---|---|
| 1 | 39 | 14 | 2.0 |
| 2 | 43 | 21 | 2.5 |
| 3 | 47 | 18 | 2.1 |
| 4 | 44 | 30 | 2.8 |

TABLE 1-continued

| Example | S.S.* in m²/g 900° C. | S.S.& in m²/g 1000° C. | OSC** in ml O₂/g |
|---|---|---|---|
| 5 | 40 | 21 | 2.8 |
| 6 | 49 | 38 | 2.1 |
| 7 | 43 | 31 | >2 |
| 8 | 58 | 37 | 2.2 |

TABLE 2

| Example | S.S.* in m²/g 900° C. | OSC** in ml O₂/g |
|---|---|---|
| 9, Comparative | 39 | 1.1 |
| 10, Comparative | 22 | 1.3 |
| 11 | 40 | 2.8 |

*S.S.: Specific surface after calcination under air for 6 hours at the temperature shown
**OSC: Oxygen storage capacity

What is claimed is:

1. Composition comprising a cerium oxide and a zirconium oxide in a cerium/zirconium atomic proportion of at least 1, wherein the composition exhibits a specific surface, after calcination for 6 hours at 900° C., of at least 35 m²/g and an oxygen storage capacity at 400° C. of at least 1.5 ml of O₂/g.

2. Composition according to claim 1, wherein the composition exhibits a specific surface, after calcination for 6 hours at 900° C., of at least 40 m²/g.

3. Composition according to claim 1, wherein the composition exhibits a specific surface, after calcination for 6 hours at 1000° C., of at least 14 m²/g.

4. Composition according to claim 1, wherein the composition exhibits an oxygen storage capacity at 400° C. of at least 1.8 ml of O₂/g.

5. Composition according to claim 1, wherein the composition exhibits an oxygen storage capacity at 400° C. of at least 2.5 ml of O₂/g.

6. A solid solution containing the composition according to claim 1.

7. Process for the preparation of a composition according to claim 1, in which a mixture is prepared in liquid medium containing at least a cerium compound and a zirconium compound; the mixture is heated; a precipitate obtained is recovered and this precipitate is calcined, wherein the mixture is prepared by using a zirconium solution which is such that the amount of base necessary to reach the equivalent point during an acid/base titration of this solution confirms the condition that, as a molar ratio, $OH^-/Zr \leq 1.65$.

8. Process according to claim 7, wherein a zirconyl nitrate obtained by attack of nitric acid on a zirconium carbonate is used as the zirconium solution.

9. Process according to claim 7, wherein the zirconium solution is such that the amount of base confirms the condition that, as a molar ratio, $OH^-/Zr \leq 1.5$.

10. Process according to claim 7, wherein the compounds comprise a salt of these compounds.

11. Coating with catalytic properties, comprising a composition according to claim 1 on a support chosen from the group consisting of:
   alumina, titanium oxide, cerium oxide, zirconium oxide, silica, spinel, zeolite, silicate, crystalline silicoaluminium phosphate or crystalline aluminium phosphate type.

12. Catalytic system comprising a coating based on a composition according to claim 1 deposited on a substrate.

13. As a use of a composition, treating exhaust gas from internal combustion engines with the composition of claim 1.

14. As a use of a composition, incorporating the composition of claim 1 in the manufacture of a catalyst for automobile afterburning.

15. Composition according to claim 1, wherein the composition is composed essentially of the cerium oxide and the zirconium oxide.

16. Composition according to claim 1, wherein the composition exhibits a specific surface, after calcination for 6 hours at 900° C., of at least 45 m$^2$/g.

17. Composition according to claim 1, wherein the composition exhibits a specific surface, after calcination for 6 hours at 1000° C., of at least 20 m$^2$/g.

18. Composition according to claim 1, wherein the composition exhibits a specific surface, after calcination for 6 hours at 1000° C., of at least 30 m$^2$/g.

19. Composition according to claim 1, wherein the composition exhibits an oxygen storage capacity at 400° C. of at least 2 ml of O$_2$/g.

20. Composition comprising a cerium oxide, a zirconium oxide and a yttrium oxide in a cerium/zirconium atomic proportion of at least 1, wherein the composition exhibits a specific surface, after calcination for 6 hours at 900° C., of at least 35 m$^2$/g and an oxygen storage capacity at 400° C. of at least 1.5 ml of O$_2$/g.

21. Composition of claim 20, wherein the composition is composed essentially of the cerium oxide, the zirconium oxide and the yttrium oxide.

22. Composition according to claim 20, wherein the composition exhibits a specific surface, after calcination for 6 hours at 900° C., of at least 40 m$^2$/g.

23. Composition according to claim 20, wherein the composition exhibits a specific surface, after calcination for 6 hours at 900° C., of at least 45 m$^2$/g.

24. Composition according to claim 20, wherein the composition exhibits a specific surface, after calcination for 6 hours at 1000° C., of at least 14 m$^2$/g.

25. Composition according to claim 20, wherein the composition exhibits a specific surface, after calcination for 6 hours at 1000° C., of at least 20 m$^2$/g.

26. Composition according to claim 20, wherein the composition exhibits a specific surface, after calcination for 6 hours at 1000° C., of at least 30 m$^2$/g.

27. Composition comprising a cerium oxide and a zirconium oxide, in a cerium/zirconium atomic proportion of at least 1, and at least one oxide chosen from scandium oxide and rare-earth metal oxides with the exception of cerium oxide, wherein the composition exhibits a specific surface, after calcination for 6 hours at 900° C., of at least 45 m$^2$/g.

28. Composition according to claim 27, wherein the composition exhibits an oxygen storage capacity at 400° C. of at least 1.5 ml of O$_2$/g.

29. Composition according to claim 28, wherein the composition exhibits an oxygen storage capacity at 400° C. of at least 1.8 ml of O$_2$/g.

30. Composition according to claim 28, wherein the composition exhibits an oxygen storage capacity at 400° C. of at least 2 ml of O$_2$/g.

31. Composition according to claim 28, wherein the composition exhibits an oxygen storage capacity at 400° C. of at least 2.5 ml of O$_2$/g.

32. Composition according to claim 27, wherein the rare-earth metal is lanthanum, neodymium or praseodymium.

33. Composition of claim 27, wherein the composition is composed essentially of the cerium oxide, the zirconium oxide, and the at least one oxide chosen from scandium oxide and rare-earth metal oxides with the exception of cerium oxide.

34. Composition comprising a cerium oxide and a zirconium oxide, in a cerium/zirconium atomic proportion of at least 1, and at least one oxide chosen from scandium oxide and rare-earth metal oxides with the exception of cerium oxide, wherein the composition exhibits a specific surface, after calcination for 6 hours at 900° C., of at least 35 m$^2$/g and an oxygen storage capacity at 400° C. of at least 1.5 ml of O$_2$/g.

35. Composition according to claim 34, wherein the composition exhibits a specific surface, after calcination for 6 hours at 900° C., of at least 40 m$^2$/g.

36. Composition according to claim 34, wherein the composition exhibits a specific surface, after calcination for 6 hours at 900° C., of at least 45 m$^2$/g.

37. Composition according to claim 34, wherein the composition exhibits a specific surface, after calcination for 6 hours at 1000° C., of at least 14 m$^2$/g.

38. Composition according to claim 34, wherein the composition exhibits a specific surface, after calcination for 6 hours at 1000° C., of at least 20 m$^2$/g.

39. Composition according to claim 34, wherein the composition exhibits a specific surface, after calcination for 6 hours at 1000° C., of at least 30 m$^2$/g.

40. Composition according to claim 34, wherein the composition exhibits an oxygen storage capacity at 400° C. of at least 1.8 ml of O$_2$/g.

41. Composition according to claim 34, wherein the composition exhibits an oxygen storage capacity at 400° C. of at least 2 ml of O$_2$/g.

42. Composition according to claim 34, wherein the composition exhibits an-oxygen storage capacity at 400° C. of at least 2.5 ml of O$_2$/g.

* * * * *